United States Patent [19]

Ishizaki et al.

[11] Patent Number: 4,839,055
[45] Date of Patent: Jun. 13, 1989

[54] METHOD FOR TREATING BLOOD AND APPARATUS THEREFOR

[75] Inventors: Makoto Ishizaki, Sendai; Takateru Sato, Kurashiki; Soichi Tanaka, Tokorozawa; Keiki Kariu, Sagamihara, all of Japan

[73] Assignees: Kuraray Co., Ltd.; Kawasumi Laboratories, Inc., both of Japan

[21] Appl. No.: 868,267

[22] Filed: May 29, 1986

[30] Foreign Application Priority Data

May 31, 1985 [JP] Japan .................. 60-119369

[51] Int. Cl.$^4$ .............................. B01D 13/00
[52] U.S. Cl. .................. 210/641; 210/321.84; 210/321.88; 210/335; 210/651
[58] Field of Search ............... 210/641, 651, 203, 259, 210/295, 321.1, 335, 433.2, 927, 321.82, 321.83, 321.84, 321.85, 321.86, 321.87, 321.88, 321.89, 314; 604/4-6

[56] References Cited

U.S. PATENT DOCUMENTS 4,125,462 11/1978 Latty .................. 210/638
4,397,747 8/1983 Ikeda .................. 210/641
4,402,940 9/1983 Nose et al. .................. 424/101

FOREIGN PATENT DOCUMENTS 150695 6/1981 Japan .
150696 6/1981 Japan .

OTHER PUBLICATIONS

Amicon Publication No. 403, Amicon Corp., Lexington, Mass., pp. 6 and 7.
Oda, T., Therapeutic Plasmapheresis (v), Proceedings of the 5th Symposium on Therapeutic Plasmapheresis, 6/1/85, pp. 403–410, Tokyo.
Oda, T., Therapeutic Plasmapheresis (i), Proceedings of the 1st Symposium on Therapeutic Plasmapheresis, 6/20/81, Tokyo, pp. 1–14.

Primary Examiner—W. Gary Jones
Attorney, Agent, or Firm—Kramer, Brufsky & Cifelli

[57] ABSTRACT

A method for treating a blood which comprises:
separating the blood withdrawn from a patient's body with a first membrane into a condensed blood fraction containing human blood plasma immunoglobulin M, and a plasma fraction; separating the plasma fraction with a second membrane into low molecular weight protein and high molecular weight protein containing human blood plasma immunoglobulin G; and mixing the condensed blood and the low molecular weight protein with a substitute liquid to return the combined liquid into the patient's body; said first and second membranes containing specific sizes of micropores uniformly distributed on at least one surface of the membrane, and having a specific permeability of albumin and specific permeability of human blood plasma immunoglobulin M or G. The method and apparatus specifically can remove only a harmful antibody from a positive patient in a crossmatch test after DST, whereby a transplantation surgery of a living-related kidney can be safely carried out.

4 Claims, 1 Drawing Sheet

METHOD FOR TREATING BLOOD AND APPARATUS THEREFOR

FIELD OF THE INVENTION

The present invention relates to a method for efficiently separating and removing human blood plasma immunoglobulin G in a blood, and an apparatus therefor. More particularly, it relates to a method for specifically removing of immunoglobulin G region containing a lymphocytotoxin from a patient, who shows positive in a crossmatch test (the test for an antibody of a kidney receptor, which antibody is reacted with a blood and lymphocyte of a donor) after a donor-specific blood transfusion (DST), and making kidney transplantation possible, and an apparatus therefor.

DESCRIPTION OF THE PRIOR ART

Prior to the transplantation of a living-related kidney, there has been carried out donor-specific blood transfusion in order to depress the rejection based on a transplantation surgery. However, this method may produce a harmful antibody in the patient after blood transfusion. In such a patient, rejection may be induced after a transplantation surgery.

It is known that the harmful antibody mainly exists in an immunoglobulin G fraction of immunoglobulin. Therefore, some patients, who show positive in a crossmatch test, have been subject to blood plasma substitution method and double filtration plasmapheresis to remove a blood plasma before kidney transplantation.

However, said blood plasma substitution method involves a high risk of the incidence of hepatitis due to the substitution of a large amount of a lyophilized blood plasma for a blood plasma.

On the other hand, although the double filtration plasmapheresis can remove immunoglobulin G (hereinafter, expressed as "IgG"), it also removes various ordinary proteins having a molecular weight more than that of IgG region, particularly blood coagulation proteins such as fibrinogen. Therefore, the method causes an extraordinary of blood coagulation ability after or directly after a surgical operation to induce a difficulty of hemostasis, so that there is a high risk of death of a patient. Then, it is deemed remarkably dangerous to subject a positive patient in a crossmatch test to a transplantation surgery of a kidney after removing a harmful antibody, and hence, actually such treatment is hardly carried out at the present.

OBJECT OF THE INVENTION

An object of the present invention is to provide a method for treating a blood which specifically removes only a harmful antibody or mainly human blood plasma IgG from a positive patient in a crossmatch test after DST, whereby a transplantation surgery of a living-related kidney can be safely carried out.

Another object of the present invention is to provide an apparatus for treating a blood which can specifically remove the above harmful antibody from a positive patient in a crossmatch test.

A further object of the present invention is to treat a patient suffering from various diseases by removing a specific fraction of a blood, which cause various diseases.

SUMMARY OF THE INVENTION

This invention provides a method for treating a blood which comprises:

separating the blood withdrawn from a patient's body with a first membrane into a condensed blood fraction containing human blood plasma immunoglobulin M, and a plasma fraction;

separating the plasma fraction with a second membrane into low molecular weight protein and high molecular weight protein containing human blood plasma immunoglobulin G; and mixing the condensed blood and the low molecular weight protein with a substitute liquid to return the combined liquid into the patient's body;

said first membrane containing micropores having an average pore diameter of 0.005-0.45 micron uniformly distributed on at least one surface of the membrane, and having a permeability of albumin of not less than 50% and permeability of human blood plasma immunoglobulin M of not more than 40%;

said second membrane containing micropores having an average pore diameter of 0.005-0.20 micron uniformly distributed on at least one surface of the membrane, and having a permeability of albumin of 30-70% and a permeability of human blood plasma immunoglobulin G of 10-50%.

This invention also provides an apparatus for treating a blood having an extracorporeal circuit of the blood which comprises:

a first filter means for separating the blood withdrawn from a patient's body into a condensed blood fraction containing human blood plasma immunoglobulin M and a plasma fraction;

a second filter means for further separating the plasma fraction into low molecular weight protein and high molecular weight protein containing human blood plasma immunoglobulin G; and a mixing means for mixing the condensed blood and the low molecular weight protein to return the combined liquid into the patient's body;

said first filter means composed of a specific permeable membrane containing micropores having an average pore diameter of 0.005-0.45 micron uniformly distributed on at least one surface of the membrane, and having a permeability of albumin of not less than 50% and permeability of human blood plasma immunoglobulin M of not more than 40%;

said second filter means composed of a specific permeable membrane containing micropores having an average pore diameter of 0.005-0.20 micron uniformly distributed on at least one surface of the membrane, and having a permeability of albumin of 30-70% and a permeability of human blood plasma immunoglobulin G of 10-50%.

According to the present invention, only IgG, which is a lymphocytotoxin produced in a positive patient in a crossmatch test after DST, is selectively removed, and the other various ordinary proteins are returned into the patient's body. Therefore, firstly there can be safely carried out the transplantation surgery of a kidney for a positive patient in a crossmatch test after DST, who has been deemed to be unbearable on the transplatation surgery of a kidney, by using of two kinds of filters which contain specific permeable membranes having a different size of microporous.

Further, by using the method and the apparatus of the present invention, there can be also carried out the treatment of various diseases such as rheumatoid arthritis, systemic lupus erythematosus, multiple myeloma, rheusus incompatibility, thrombocytopenic purpura, myasthemia gravis, goodpasture syndrome, penphigus vulgaris, polymeuropathy, autoimmue hemolytic anemia, and the like without decreasing the ordinary fractions of a blood.

DETAILED DESCRIPTION OF THE INVENTION

Figure 1:
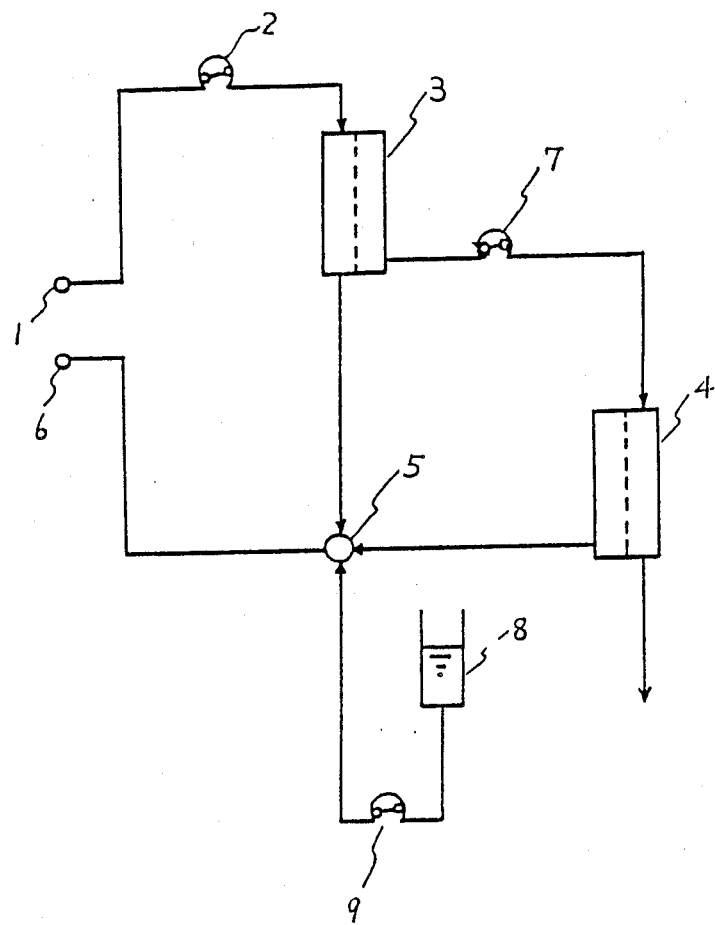
FIG. 1 is a flowsheet of an embodiment of the present invention.

The present invention is further illustrated according to the embodiment shown in FIG.1.

FIG. 1 is the flowsheet which shows an essential construction of the apparatus for treating a blood of the present invention. The apparatus shown in FIG. 1 is illustrated according to the flow direction of a blood.

The blood is introduced into the apparatus via a blood inlet 1 into a blood introducing section, and transferred to a first filter 3, if desired, by a pump 2 such as a roller pump. When the blood is directly introduced, a shunt (not shown) is usually used. In the first filter 3, the blood is separated into a condensed blood containing human immunoglobulin M (hereinafter expressed as "IgM"), and a blood plasma by means of a first specific permeable membrane.

Then, the blood plasma separated by the first filter 3 is transferred into a second filter 4, if desired, by a pump 7 such as a roller pump. In the second filter 4, high molecular weight protein containing IgG is removed from the blood plasma as a filtration residue, and withdrawn through the circuit of the blood.

On the other hand, the clear filtrated blood plasma is transferred into a mixer 5, which combines the plasma from the second filter 4 with the condensed blood containing human IgM from the first filter 3 and a substitute fluid. The substitute fluid is transferred into the mixer 5 from a reservoir 8 via a pump 9 in an equivalent amount to the high molecular weight protein containing IgG, which is withdrawn from the second filter 4. The above combined blood is returned into the patient's body via a blood outlet 6.

The first specific permeable membrane contained in the first filter 3 in the present invention prevents the permeation of a corpuscular fraction as well as a high molecular proteins such as fibrinogen and blood plasma IgM (molecular weight: about 950,000), and on the other hand, the membrane can substantially permeates all of the protein fractions such as blood plasma IgG (molecular weight: about 160,000) and albumin in a blood plasma. Then, there is used a membrane, which contains micropores having an average pore diameter of 0.005–0.45 micron uniformly distributed on at least one surface of the membrane, and has a permeability of albumin of not less than 50 %, preferably not less than 95% and a permeability of human blood plasma IgM of not more than 40%, preferably not more than 20%. U. S. Pat. 4,402,940 discloses a method for preparing the above membrane from an ethylene-vinyl alcohol copolymer as follows.

The ethylene-vinyl alcohol copolymer membrane is obtained by dissolving an ethylene-vinyl alcohol copolymer with an ethylene content of 10 to 90 mol% in a solvent comprising at least one compound selected from the group of dimethyl sulfoxide, dimethylacetamide, methylpyrrolidone and pyrrolidone, to obtain a solution with a polymer concentration (C) of 10 to 40% (by weight), and by feeding the resulting polymer solution into coagulation bath chiefly consisting of water, to form a membrane.

Selection of coagulation temperature is especially important for obtaining a membrane suitable for a method of the present invention. A close relation exists between the polymer concentration (C) and coagulation temperature (T) and the desired ethylene-vinyl alcohol copolymer membrane can be obtained when the relation is defined in the following range;

$C-10 \leq T \leq C+30$, preferably $C-8 \leq T \leq C+15$

Solvents for dissolving said ethylene-vinyl alcohol copolymer may be a monohydric alcohol such as methanol or ethanol, a polyhydric alcohol such as ethylene glycol, propylene glycol, or glycerol, phenol, m-cresol, methylpyrrolidone, formic acid, and those containing water. Amount these the one selected from the group of dimethyl sulfoxide, dimethyl-acetamide, methylpyrrolidone, pyrrolidone and mixture of said substances are suitable for manufacturing a separating membrane having well-balanced water and solute permeabilities which is to be obtained in a method of the present invention. Especially, dimethyl sulfoxide which can dissolve the ethylene-vinyl alcohol copolymer therein at a high level is preferable.

In dissolving the ethylene-vinyl alcohol copolymer in said solvent, its concentration is in the range of 10 to 40% by weight, preferably 15 to 35% by weight. Further, the temperature of the polymer solution is 0° to 120°C., preferably 5° to 67°C. When the temperature of the solution is above said range, the polymer is liable to be denatured, while when it is below said level, the viscosity of the stock solution becomes so high that the membrane formation becomes difficult.

In the coagulation bath, an aqueous medium is used as a coagulating agent. The aqueous medium may be water alone, an aqueous solution containing a water-miscible organic solvent, usually the same as one used for preparing the polymer solution in a range of not more than 70% by weight, or said aqueous solution to which is further added an inorganic salt such as Glauber's salt. The membrane can be manufactured above a gelation temperature of the stock solution in a wet coagulation process or in a dry/wet process where the stock solution is fed into a coagulation bath after passing air or solvent vapor. After the coagulation, wet heat processing, elongation, drying or the like, can be employed if necessary. The membrane can be used in a wet state, or after dried, and it is desirable to use it after drying in view of easy handling. Methods for drying the membrane may be drying under normal or reduced pressure below a glass transition point of the ethylene-vinyl alcohol copolymer, more preferably at around room temperature, freeze-drying where water contained in the wet membrane is sublimated under reduced pressure after freezing the membrane with liquid nitrogen, etc., or an organic solvent replacement method where a water-miscible organic solvent is first replaced for water contained in the membrane and then the solvent is removed by vaporization.

In the organic solvent replacement method, a permeable membrane which maintains its permeable performance is obtained by dipping the wet membrane in a water-miscible organic solvent to replace for an aqueous medium present on the surface or inside of the membrane, and drying the resulting membrane below a glass transition point of the ethylene-vinyl alcohol copolymer, preferably at room temperature, under normal or reduced pressure. In this method, lower aliphatic alcohol or ketones having 1 to 5 carbon atoms are preferred organic solvents and, for example, methanol, ethanol, amyl alcohol, acetone, methyl ethyl ketone, or diethyl ketone can be used. Among them, acetone is particularly preferable. Drying of the resulting membrane after the replacement process is carried out below a glass transition point of the copolymer. In another way where said organic solvent is not used for replacing for water, a membrane which can maintain the permeability after formation is obtained by treating the undried membrane below 50°C. with an aqueous or alcoholic solution of a polyhydric aliphatic alcohol containing 2 to 4 carbon atoms or an adduct obtained by adding 1 to 20 mol of ethylene oxide to said alcohol, and then drying the resulting membrane below 50°C.

In this method, the resulting membrane contains, in a ratio of 20 to 120%, the polyhydric alcohol or ethylene oxide adduct of said alcohol which can be easily removed from the membrane by washing after its construction into a module and before use. The polyhydric aliphatic alcohols having 2 to 4 carbon atoms may be ethylene glycol, diethylene glycol, propylene glycol, 1,3-butanediol, 1,4-butanediol, or glycerol, and glycerol is especially desirable. Said polyhydric aliphatic alcohols may also be added to a coagulating liquid to be used in a wet method for manufacturing the membrane and thus incorporated in the resulting membrane.

Further, in order to steadily separate the blood with no harm of the blood by the first filter 3, it is necessary to control the pressure difference between the inlet and outlet of the blood in a range of 10-60 mmHg.

Then, the second specific permeable membrane contained in the second filter 4 in the present invention prevents the permeation of a high molecular weight protein containing blood plasma IgG in the blood plasma fraction which is separated at the first filter 3, and on the other hand, the second membrane can substantially permeate all of the low molecular protein containing albumin in the blood plasma. Then, there is used the second membrane which contains micropores having a average pore size of 0.005-0.20 micron uniformly distributed on at least one surface of the membrane, and has a permeability of albumin of 30-70%, preferably not less than 80% and a permeability of human blood plasma IgG of 10-50%, preferably not more than 30%. Such membranes are conventional and disclosed, for example, in the Japanese Journal of Medical Instrumentation, Vol 149, Supplement, p. 259-261 (1979), and Japanese Patent Laid Open Publication Nos. 75163/1981 and 75164/1981. Such membrane can be also obtained in the same manner as described above with respect to the first membrane expect for using the coagulation temperature of the following range:

$$C-31 \; 15 \leq T \leq C-5$$

The membranes used in the present invention may be flat membranes, a hollow fiber membranes or constitute membrane modules.

The membranes used in the first and second filter means in the present invention may have the construction which contains uniformly distributed micropores in the both side of the surfaces thereof, and said micropores pass from the one surface to the other.

When the membrane is a hollow fiber membrane, it may have the construction composed of a dense microporous layer of the outside of the membrane, and a porous layer of the inner layer and the inside of the membrane. It may also have the construction composed of a dense microporous layer of the inside, and a porous layer of the inner layer and the outside. Further, it may also have the construction composed of a dense microporous layer of the inside and outside, and a porous layer of the inner layer. Among them, the membrane of the non-symmetrical construction having porous layers in the inner layer and the inside of the membrane (or the side against the flow direction of the blood) is most preferable because the porous layers in the inner layer and the inside of the membrane fill the role of a pre-filter, prevent the clogging of the dense microporous layer in the other side of the surface, and show a steadily high cut-off performance (ability to obtain fine fractions) and a high water permeability.

The specific permeable membranes used in the present invention may be made from vinyl alcohol polymers such as a polyvinyl alcohol copolymer and an ethylene-vinyl alcohol copolymer, polyacrylonitrile, polymethyl methacrylate, cellulose (cupro-ammonium cellulose, acetyl cellulose, etc.) polysulfone, or the like. Among them, the ethylene-vinyl alcohol copolymer is preferred.

The membranes used in the present invention may be assembled into the first and second filter means in the conventional manners.

The mixer 5 in the present invention is used for combining the filtrated blood plasma and the condensed blood, and as a mixer a drip chamber is usually used.

The substitute liquid may be usually a blood plasma protein preparation. A lyophilized blood plasma is preferably used in order to prevent hemorrhagic diathesis due to the decreasing of fibrinogen.

In order to selectively separate IgG from the blood of the patient in the application of the apparatus of the present invention for the positive patient in crossmatch test, it is preferable that the blood plasma subjected to one treatment is in an amount of ½-2 times of that of the patient. When the amount of the treated blood plasma in one treatment is less than ½ of that of the patient, it induces an insufficient decreasing of antibody titre. On the other hand, when the amount of the treated blood plasma in one treatment is over 2 times of that of the patient, in spite of the decreasing of an antibody, it undesirably causes a remarkable physical burden of the patient for long term of the treatment. When the antibody titre can not be decreased sufficiently in one treatment, it is preferable to take several treatments at intervals.

Preferred amount of a waste liquid from the second filter means is in the range of 0-30% based on the amount of the treated blood plasma according to the characteristics of the blood plasma and the state of the clogging in the filter means. When the amount of the waste liquid is over such range, it undesirably requires a large amount of the substitute liquid.

ADVANTAGES OF THE INVENTION

According to the present invention, there can be selectively removed IgG or a lymphocytotoxin without the decreasing of ordinary proteins such as fibrinogen in the blood of the positive patient in a crossmatch test after DST, whereby there can be safely operated without hemorrhagic diathesis in a transplantation surgery as well as after the transplantation. Further, according to the present invention, there can be treated patients suffering from various diseases by removing specific fractions of a blood, which cause the diseases.

The present invention is further illustrated by the following examples.

EXAMPLE 1

A first filter (manufactured by Kuraray Co., Ltd.; EVAFLUX 4A, membrane area: 2 m$^2$) and a second filter (manufactured by Kuraray Co., Ltd.; EVAFLUX 2A, membrane area: 2 m$^2$) was assembled into an apparatus shown by the flowsheet in FIG. 1 (manufactured by Kuraray Co., Ltd.; double filtration plasmapheresis system (KM-8500).

The first filter 3 contained non-symmetrical hollow fiber membranes (membrane thickness: 50 micron, inner diameter: 200 micron) of an ethylene-vinyl alcohol type copolymer, which had micropores having an average pore diameter of 0.005-0.45 micron uniformly distributed on at least one surface of the membrane, and had a permeability of albumin of not less than 50%, permeability of IgM of not more than 40% and water permeability of not less than 100 ml/m$^2$.hr.mmHg;

The second filter 4 contained non-symmetrical hollow fiber membranes (membrane thickness: .50 micron, inner diameter: 200 micron) of an ethylene-vinyl alcohol type copolymer, which had micropores having an average pore diameter of 0.005-0.20 micron uniformly distributed on at least one surface of the membrane, and had a permeability of albumin of 30-70% and a permeability of IgG of 10-50%.

Using of a bovine blood added with ACD, there was carried out a in vitro test. The bovine blood (3 liter), which hematocrit value was evaluated to 40%, was charged into a beaker in a constant temperature bath. The bovine blood was introduced with stirring to the apparatus via inlet 1 and fed to the first filter 3 at a rate of 100 ml/min through a pump 2. Then, the blood plasma was withdrawn from the first filter 3 at a rate of 30 ml/min, and fed to the second filter 4 through a pump 7. In the second filter, high molecular weight protein was thrown away at a rate of 6 ml/min. The substitute liquid of a physiological saline solution equivalent to the amount of the waste liquid was supplied from a reservoir 8 to a mixer 5 via a pump 9. In the mixer 5, the substitute liquid as combined with the condensed blood separated by the first filter 3 and the low molecular weight protein separated by the second filter 4, and returned to the beaker in the constant temperature bath via an outlet 6. The total amount of the blood plasma fed to the second filter 4 was 2 liter.

The resulting change of the protein concentration in the bovine blood and the rate of decrease thereof are shown in Table 1.

TABLE 1

|  | Before Treatment (mg/dl) | After Treatment (mg/ml) | Rate of Decrease (%) |
| --- | --- | --- | --- |
| Albumin | 4,100 | 2,250 | 45 |
| IgG | 1,400 | 730 | 48 |

TABLE 1-continued

|  | Before Treatment (mg/dl) | After Treatment (mg/ml) | Rate of Decrease (%) |
| --- | --- | --- | --- |
| Fibrinogen | 1,200 | 710 | 37 |

EXAMPLE 2

The positive patient in a crossmatch test after DST was subjected to the treatment of a blood at total six times by using of the apparatus of Example 1 with the filters of Example 1. At one treatment, the rate of the blood was 100 ml/min, and the rate of a filtrated blood plasma was 30 ml/min. The rate of the waste high molecular weight protein from the second filter was 7 ml/min. A lyophilized blood plasma was used as a substitute liquid. Lymphocytotoxin was decreased with the times of the treatment, and the crossmatch test became negative by six times of the treatments. When the crossmatch test showed negative, a transplantation surgery of a kidney was carried out and the implantation of the kidney was successfully perfected without rejection, bleed and infection. By the present apparatus, IgG, IgM and fibrinogen in the blood after the treatment were removed in an ratio of 42%, -9% and 2% respectively based on those before the treatment. The increasing of fibrinogen after the treatment is deemed to be caused by the use of a lyophilized blood plasma as a substitute liquid.

What is claimed is:

1. A method for selectively removing IgG from blood which comprises:

separating the blood withdrawn from a patient's body with a first membrane into a blood fraction containing human blood plasma immunoglobulin M, and a plasma fraction;

separating the plasma fraction with a second membrane into a low molecular weight protein fraction and a high molecular weight protein fraction containing human blood plasma immunoglobulin G; and mixing the blood fraction and the low molecular weight protein fraction with a substitute liquid to return the combined liquid into the patient's body;

said first membrane containing micropores, exhibiting an average pore diameter of 0.005-0.45 micron, uniformly distributed on at least one surface of the membrane, and having a permeability of albumin of not less than 50% and a permeability of human blood plasma immunoglobulin M of not more than 40%;

said second membrane containing micropores, exhibiting an average pore diameter of 0.005-0.20 micron, uniformly distributed on at least one surface of the membrane, and having a permeability of albumin of 30-80% and a permeability of human blood plasma immunoglobulin G of 10-50%.

2. A method according to claim 1, wherein the blood plasma subjected to one treatment is in an amount of ½ times of that of the patient.

3. A method according to claim 1, wherein the first membrane has a permeability of albumin of not less than 95% and permeability of human blood plasma immunoglobulin M of not more than 20%.

4. A method according to claim 1, wherein the first and second membranes are made of an ethylene-vinyl alcohol copolymer.

* * * * *